United States Patent
Willis

(10) Patent No.: US 12,042,471 B2
(45) Date of Patent: *Jul. 23, 2024

(54) OCULAR TREATMENTS FOR NEUROLOGICAL AND NEUROPSYCHIATRIC DISORDERS

(71) Applicant: PhotoPharmics, Inc., American Fork, UT (US)

(72) Inventor: Gregory Lynn Willis, Woodend (AU)

(73) Assignee: PhotoPharmics, Inc., American Fork, UT (US)

( * ) Notice: Subject to any disclaimer, the term of this patent is extended or adjusted under 35 U.S.C. 154(b) by 408 days.

This patent is subject to a terminal disclaimer.

(21) Appl. No.: 15/794,886

(22) Filed: Oct. 26, 2017

(65) Prior Publication Data

US 2018/0140561 A1 May 24, 2018

Related U.S. Application Data

(63) Continuation of application No. 12/666,960, filed as application No. PCT/AU2008/000955 on Jun. 30, 2008, now Pat. No. 9,827,210.

(30) Foreign Application Priority Data

Jun. 29, 2007 (AU) .................................. 2007903747

(51) Int. Cl.
| | |
|---|---|
| A61K 31/13 | (2006.01) |
| A61K 9/00 | (2006.01) |
| A61K 9/48 | (2006.01) |
| A61K 9/51 | (2006.01) |
| A61K 31/165 | (2006.01) |
| A61K 31/4515 | (2006.01) |
| A61K 31/454 | (2006.01) |
| A61K 31/5415 | (2006.01) |
| A61P 25/16 | (2006.01) |

(52) U.S. Cl.
CPC ............ *A61K 31/13* (2013.01); *A61K 9/0048* (2013.01); *A61K 31/165* (2013.01); *A61K 31/4515* (2013.01); *A61K 31/454* (2013.01); *A61K 31/5415* (2013.01); *A61K 9/0051* (2013.01)

(58) Field of Classification Search
CPC .. A61K 31/13; A61K 9/48; A61K 9/51; A61P 25/16

See application file for complete search history.

(56) References Cited

U.S. PATENT DOCUMENTS

| | | | | |
|---|---|---|---|---|
| 4,565,821 A | * | 1/1986 | Chiou .................. | A61K 31/445 514/317 |
| 4,654,361 A | * | 3/1987 | Samples ................ | A61K 31/40 514/419 |
| 5,767,162 A | | 6/1998 | Weber et al. | |
| 6,331,313 B1 | * | 12/2001 | Wong .................... | A61K 9/0051 424/427 |
| 9,827,210 B2 | * | 11/2017 | Willis ................... | A61K 9/0048 |
| 2002/0068692 A1 | * | 6/2002 | Willis .................... | A61K 31/00 514/1 |
| 2003/0072793 A1 | | 4/2003 | Frey, II et al. | |
| 2003/0087799 A1 | * | 5/2003 | Wolfart ................. | A61K 31/00 514/1 |
| 2005/0020664 A1 | | 1/2005 | Zisapel et al. | |
| 2006/0073182 A1 | * | 4/2006 | Wong .................... | A61K 9/0024 424/426 |
| 2006/0239966 A1 | * | 10/2006 | Tornoe ................. | A61K 48/005 424/93.2 |
| 2007/0049576 A1 | | 3/2007 | Barlow et al. | |

FOREIGN PATENT DOCUMENTS

| | | | |
|---|---|---|---|
| CN | 1569219 | * | 1/2005 |
| EP | 1632238 A1 | | 3/2006 |
| JP | 05507916 A | | 11/1993 |
| JP | 2002-531490 A | | 9/2002 |
| JP | 2002-541105 A | | 12/2002 |
| JP | S6322013 B2 | | 9/2018 |
| WO | 199119482 A1 | | 12/1991 |
| WO | 2000033814 A2 | | 6/2000 |
| WO | 2000059504 A1 | | 10/2000 |
| WO | 200076454 A2 | | 12/2000 |
| WO | 02/28347 A2 | | 4/2002 |
| WO | 2002085248 A3 | | 10/2002 |
| WO | 2006/082588 A2 | | 8/2006 |
| WO | 2007020672 A3 | | 2/2007 |

OTHER PUBLICATIONS

Xu et al. CN1569219 . English Translation. (Year: 2005).*
Laudon et al. ("N-(3,5-dinitrophenyl)-5-methoxytryptamine, a novel melatonin antagonist: effects on sexual maturation of the male and female rat and on oestrous cycles of the female rat." Journal of Endocrinology (1988); 116(1):43-53. https://doi.org/10.1677/joe.0.1160043). (Year: 1988).*
Attar-Levy et al., "Seasonal Affective Disorders: A New Clinical Category?" *Presse Med* 19(10): 465-470 (1990).
Brocks, "Anticholinergic drugs used in Parkinson's disease: An overlooked class of drugs from a pharmacokinetic persective," *J. Pharm. Pharmaceut. Sci.*, 2(2): 39-46 (1999).

(Continued)

*Primary Examiner* — Jeffrey S Lundgren
*Assistant Examiner* — Chris E Simmons
(74) *Attorney, Agent, or Firm* — DENTONS Durham Jones Pinegar

(57) ABSTRACT

A method for the treatment and/or prophylaxis of a neurological and/or neuropsychiatric disorder associated with altered dopamine function comprising administering to the eye of a patient in need thereof an effective amount of an agent that modulates neurotransmitter production or function.

18 Claims, 13 Drawing Sheets

(56) References Cited

OTHER PUBLICATIONS

Hornykiewicz, "Commentary; Parkinson's Disease and It's Chemotherapy," *Biochemical Pharmacology*, 24: 1061-1065 (1975).

Mosbach et al., "Phototherapy as a Treatment for Sleep Disorder in Parkinson's Disease: A Case Study," *Neurology*, 43(4): Supp. 2 (1993).

Terman, "Evolving Applications of Light Therapy," *Sleep Medicine Reviews*, 11: 497-507 (2007).

Ungersted et al., "Behavioral, Physiological, and Neurochemical Changes after 6-Hydroxydopamine-Induced Degeneration of the Nigro-Striatal Dopamine Neurons," *Advances in Neurology*, 5: 421-426 (1974).

Willis et al., "Orphan Neurones and Amine Excess: The Functional Neuropathology of Parkinsonism and Neuropsychiatric Disease," *Brain Research Reviews*, 27: 177-242 (1998).

Willis, "Intraocular Microinjections Repair Experimental Parkinson's Disease," *Brain Research*, 1217: 119-131 2008.

Wang, JK, "An Asian patient with intraocular lymphoma treated by intravitreal methotrexate," Jpn J Ophthalmol., (50 (5):474-478 (2006) (English Abstract only).

IP Australia as International Searching Authority, "International Search Report and Written Opinion," for application No. PCT/AU2008/000955 (Aug. 29, 2008).

\* cited by examiner

OCULAR TREATMENTS FOR NEUROLOGICAL AND NEUROPSYCHIATRIC DISORDERS

FIELD OF THE INVENTION

This invention relates to the treatment or prophylaxis of a neurological or neuropsychiatric disorder associated with altered dopamine function in a patient by administering an agent that modulates neurotransmitter production or function. The invention particularly relates to the use of an agent in the treatment or prophylaxis of a neurological or neuropsychiatric disorder associated with altered dopamine function by administering an effective amount of an agent to the eye of a patient.

BACKGROUND OF THE INVENTION

A number of neurological or neuropsychiatric disorders, such as Parkinson's disease, are regarded as being associated with altered amine function in the brain. These amines include dopamine, noradrenalin and serotonin. More particularly, a number of neurological or neuropsychiatric disorders, and especially Parkinson's disease, are associated with the altered dopamine function of neurones found in the nigro-striatal dopamine system and meso-cortical system.

The cell bodies of the neurones comprising the nigro-striatal dopamine system are located in the midbrain and comprise the substantia nigra. The axons of these neurones run in an anterior direction from the midbrain, through the lateral hypothalamus and into the forebrain, terminating in the nucleus caudatus, the globus pallidus and the putamen nucleus.

The cell bodies of the neurones comprising the meso-cortical system are located in the midbrain. The axons of these neurones run in an anterior direction from the midbrain, through the lateral hypothalamus and into the forebrain terminating in structures such as the frontal cortex, the amygdala and other frontal areas. It is thought that hallucinations, cognitive impairment and emotional changes, all of which characterises schizophrenia, are mediated by the production of excess amounts of dopamine in the meso-cortical system.

When the dopamine neurones of the nigro-striatal dopamine system undergo degeneration there is a decrease in normal synaptic transmission. The decrease in synaptic transmission is associated with a depletion of functional dopamine, which in turn decreases the communication between nigro-striatal dopamine system neurones and adjacent neurones. This is an insidious process and takes many years to occur.

In the case of Parkinson's disease, the degeneration of the dopamine neurones also leads to the gradual development of the primary symptoms of Parkinson's disease. These primary symptoms include bradykinaesia or slowness, muscular rigidity and tremor. Secondary symptoms also develop, including depression, anxiety, nocturnal movement or nocturnal myoclonus, akathesia, loss of balance, reduced arm swing, masked face, falling, seborrhea, bradylogia, impaired speech, excessive salivation, freezing, memory loss, bradyphrenia, irritability, mood swing, confusion, disorientation, loss of appetite and insomnia and sometimes excessive sleep.

The degeneration of dopamine neurones in the nigro-striatal dopamine system is believed to be causal to a number of neurological and neuropsychiatric disorders, including Parkinson's disease.

To date, therapies for such neurological and neuropsychiatric disorders are largely aimed at replacing dopamine in the nigro-striatal dopamine system.

The approach adopted to treat Parkinson's disease, and other neurological and/or neuropsychiatric disorders, has been to focus on dopamine replacement, as well as protection and repair of nigro-striatal dopamine neurones by administering dopamine precursors, dopamine agonists, catabolic enzyme inhibitors, antioxidants, foetal cells, stem cells or genetic manipulation to reinstate dopamine function of the nigro-striatal dopamine system.

Some symptomatic relief is usually experienced by the administration of drugs which increase dopamine levels in the nigro-striatal dopamine system. Such drugs include dopamine precursors such as L-dopa, dopamine agonists such as pergolide, bromocriptine or other ergot derivatives, dopamine degradative enzyme inhibitors such as COMT inhibitors or MAO inhibitors such as Comtan® or Deprenyl®. While motor impairment and other symptoms improve with treatment, with time the efficacy of these drugs decrease. When this occurs it is necessary to increase the dose of the drugs that increase dopamine to a point at which side effects become so severe that dyskinaesia and psychosis occur.

It is also possible to implant cells, including foetal or stem cells, into the substantia nigra which grow to function normally and increase dopamine levels. Cell implantation of foetal, neonatal, stem or nigro-striatal dopamine cells for the purpose of increasing dopamine levels is highly invasive and costly. Cell implantation also appears to show limited efficacy.

With the long term use of dopamine replacement, the patient develops excessive involuntary movement and begins to hallucinate, similar to the psychosis seen in schizophrenia. To counteract these side effects a second drug has to be administered, which are typically the same as those prescribed for schizophrenia. Haloperidol, spiroperidol or the atypical neuroleptics are examples of drugs that can be used to treat the psychosis produced by overdoses of dopamine replacement. Similarly, the increased use of recreational drugs, such as heroin, cannabis, ketamine, benzodiazepines and amphetamines also produce a feeling of euphoria and a "psychosis-like' state that is believed to be mediated by various brain systems including the meso-cortical system and the nigro-striatal dopamine system. To counteract the effects of these drugs the oral administration of various antipsychotic drugs is employed as treatment.

Huntington's Chorea is another disease which is genetically based and is characterised by atrophy of the corpus striatum and increased production of dopamine. The features of this disease include the expression of choriaform movements and hallucination much like those seen with dyskinaesia after dopamine replacement or like those seen in schizophrenia. To treat this disease dopamine receptor blockers and other antipsychotics are often administered systemically (orally) to treat the symptoms.

There is therefore a need to provide improved treatments for neurodegenerative and neuropsychiatric disorders associated with altered amine function.

The retina, situated at the back of the eye, contains numerous cells including, but not limited to, ganglion cells, rods, cones, Type W cells, amacrine cells and dopamine and melatonin-containing cells. One aspect of the "downstream" extension of these cells runs into the optic tract and the thalamus, through structures including the corpus quadrigemini and then onto the visual cortex. It is this pathway which is deemed responsible for processing photic information and is the system that underlies the human ability to experience sight and to possess the sense of visual perception.

A second "downstream" aspect of the extension of these retinal cells runs via the accessory optic tract, through the hypothalamus and into the midbrain where it terminates in several anatomical structures including the dorsal, medial and lateral terminal nuclei of the diencephalon.

A third "downstream" aspect of the extension of these retinal cells runs via the retinal hypothalamic tract, through the suprachiasmatic and paraventricular nuclei of the hypothalamic and other hypothalamic nuclei, through the lateral and posterior-lateral hypothalamus and medial forebrain bundle, through the midbrain, through the spinal column at the level of T1 to T3, through the superior cervical ganglia and the nerve conarii, terminating in pinealocytes of the pineal gland.

It is by the second and, in particular, the third aspect, that the mammalian organism receives diurnal/nocturnal signals from the environment. In the presence of bright light, cells of the retina are stimulated and a signal is sent along the retinal hypothalamic tract to the pineal gland, where the secretion of melatonin is regulated by this stimulus, and melatonin secretion is decreased. In the absence of light stimulation of the retina and the retinal hypothalamic tract, there is a decrease in the inhibitory signal to the pineal gland and with this the secretion of melatonin increases.

Neuroscientific studies and clinical findings that examine the role of melatonin in the occurrence of neuropsychiatric disease suggest that melatonin from the pineal gland is important in its capacity as an antioxidant. In addition, it has been reported that melatonin has an important antioxidative role in the human body and that melatonin deficiency increases with advancing age.

SUMMARY OF THE INVENTION

This invention is based on the finding that there is a mechanism involving melatonin and dopamine production located in the retina, as part of a more global system, that is involved in the aetiology, progression and expression of neurological and neuropsychiatric disorders associated with altered amine function. This is the first time that the retina, or any part of the retinal hypothalamic tract, has been found to play a role in the occurrence of Parkinson's disease or any other neurological or neuropsychiatric disorder.

Accordingly, in a first aspect the present invention provides a method for the treatment and/or prophylaxis of a neurological and/or neuropsychiatric disorder associated with altered dopamine function comprising administering to the eye of a patient in need thereof an effective amount of an agent that modulates neurotransmitter production or function.

In a second aspect, the present invention provides a use of an agent that modulates neurotransmitter production or function in the manufacture of a medicament for the treatment and/or prophylaxis of a neurological and/or neuropsychiatric disorder, wherein the medicament is administered to the eye of a patient.

In a third aspect, the present invention provides a use of an agent that modulates neurotransmitter production or function for the treatment and/or prophylaxis of a neurological and/or neuropsychiatric disorder, wherein the agent is administered to the eye of a patient.

Advantageously, small doses of agent may be used when administered to the eye of a patient such that the agent comes into contact with the retina. The use of small doses of agent may reduce the side effects that are commonly seen when large doses of therapeutic agents are administered systemically.

In one embodiment, the agent is administered such that it comes into contact with the retina. In another embodiment, administration of the agent results in modulation of melatonin production in the pineal gland The agent may be administered by intraocular injection, by intraocular perfusion, opthalmic drops or iontophoresis. In a further embodiment, the agent is administered by intraocular injection.

In another embodiment, the agent is administered into the aqueous humor, the vitreous humor or the cornea. In a further embodiment, the agent is administered into the vitreous humor. The agent may also be administered to the eye using an intraocular insert.

In one embodiment, the agent modulates the production of one or more neurotransmitters selected from acetylcholine, GABA, serotonin, dopamine, noradrenalin and melatonin, precursors thereof and/or metabolic products thereof.

Modulation of neurotransmitter production may be an increase in dopamine production, precursors thereof and/or metabolic products thereof. Modulation of neurotransmitter production may alternatively be an inhibition of melatonin production, precursors thereof and/or metabolic products thereof. Similarly modulation of neurotransmitter function may be achieved by modifying levels of neurotransmitter, for example by removing degradation pathways or reuptake, or by facilitating degradation or reuptake.

The agent may be one or more of domperidone, haloperidol, pimozide, clonazipine, sulperide, metaclopromide, ML-23, spiroperidol, haloperidol, thioxanthene, fluphenazine, lithium carbonate, thioidazine, valium, diazepam, pimozide, chlorpromazine, benzodiazepines, respiradol, quetiapine fumarate, propranolol, atenolol, melanocyte stimulating hormone (MSH), selegiline, parlodel, cogentin, Kripton, cabaser, benztropine, biperiden HCl, apomorphine, entacapone, pergolide, amantadine, L-dopa, tetrabenazine, resagaline and carbidopa, pharmaceutically acceptable salts thereof, derivatives thereof and/or prodrugs thereof.

The agent may be a melatonin antagonist, a beta adrenergic antagonist, a calcium channel blocker or melanocyte stimulating hormone (MSH).

In another embodiment, the agent is a stem cell and/or a retinal cell.

The neurological and/or neuropsychiatric disorder may be one or more of Parkinson's disease, Huntington's chorea, periodic limb movement syndrome, restless leg syndrome, nocturnal myoclonus, Tourette's syndrome, Sundowner's syndrome, REM Sleep Behaviour Disorder, schizophrenia, Pick's disease, Punch drunk syndrome, progressive subnuclear palsy, multiple systems atrophy, corticobasilar degeneration, vascular parkinsonism, Lewy body dementias, diffuse Lewy body disease, Parkinson's plus syndrome, Korsakow's syndrome (Korsakoff's syndrome), multiple sclerosis, medication-induced motor disorders, drug-induced Parkinson's disease, neuroleptics-induced Parkinson's disease, acute dystonia, stroke-post ischemic Parkinsonism, trans-ischemic attack, akathesia dyskinaesia, tardive dyskinaesia, Alzheimer's disease, dementia, depressive pseudo dementia, hydrocephalic dementia, dementia associated with Parkinson's disease, anxiety, generalized anxiety disorder, panic disorder, agoraphobia, obsessive-compulsive disorder, post-traumatic stress disorder, acute stress disorder, depression, bipolar disorder, various personality disorders, drug addiction, drug-induced psychosis and drug withdrawal.

In one embodiment, the neurological and/or neuropsychiatric disorder is Parkinson's disease.

In another embodiment, the neurological and/or neuropsychiatric disorder is one or more of drug addiction, drug-induced psychosis and drug withdrawal.

In a further embodiment, the neurological and/or neuropsychiatric disorder is one or more of schizophrenia, psychosis, dyskinaesia, Huntington's chorea, or drug addiction.

In one embodiment, the agent is administered in minute doses and volumes.

One or more further agents may also be administered sequentially, separately or simultaneously with the agent that modulates neurotransmitter production. In one embodiment, the one or more further agents is administered to the eye.

In a further embodiment, the eye of the patient may also be subjected to light therapy sequentially, separately or simultaneously with the administration of the agent that modulates neurotransmitter production.

BRIEF DESCRIPTION OF FIGURES

Preferred embodiments of the invention will now be described with reference to the following drawings, which are intended to be exemplary only, and in which.

Figure 1:
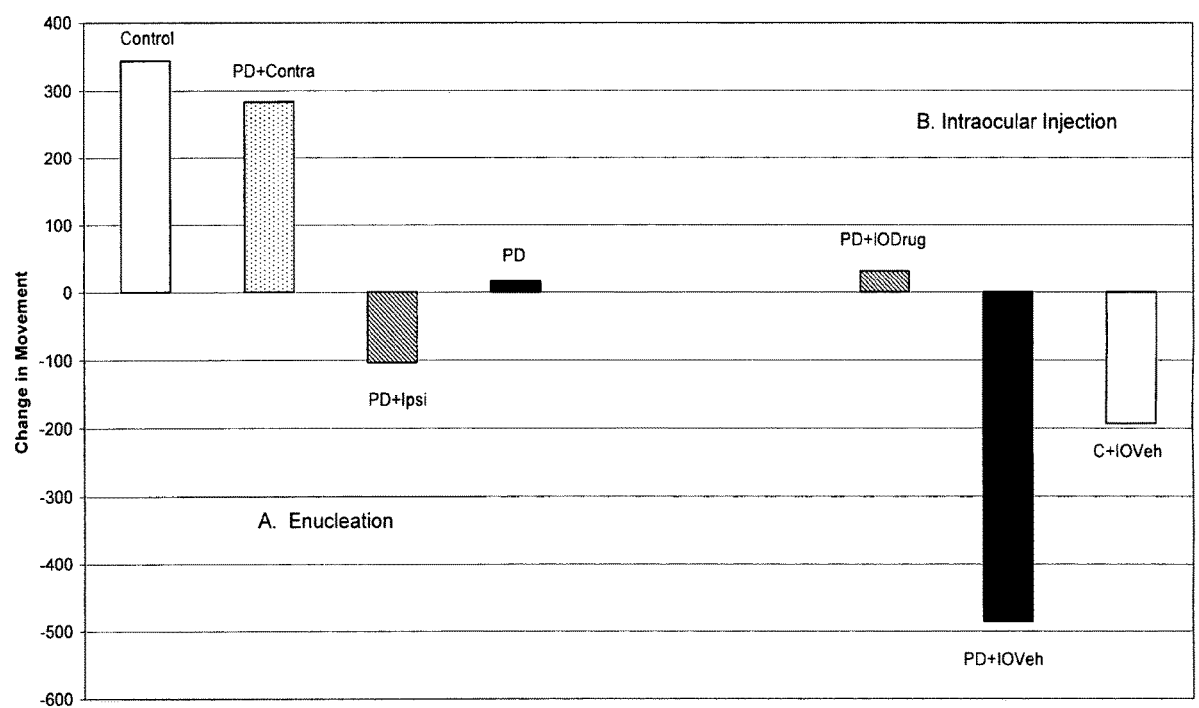
FIG. 1 is a graph showing the effect of enucleation or surgical removal of the eye of a rat, as depicted by the effect on horizontal movement in experimental Parkinson's disease (A), and showing the effect of bilateral, intraocular or intravitreal injection of ML-23 on the horizontal movement in a rat with experimental Parkinson's disease (B).

In the figures, a reference to the acute phase refers to the first 9 days, while the recovery phase refers to later than 9 days.

DETAILED DESCRIPTION OF THE INVENTION

According to one embodiment of the present invention there is provided a method for the treatment and/or prophylaxis of the symptoms of a neurological or neuropsychiatric disorder associated with altered dopamine function which comprises subjecting a patient in need of therapy which increases dopamine, by administering an agent in minute doses and volumes directly into the vitreous humor of the eye by intraocular or intravitreal injection.

According to another aspect of the present invention the injection of any substance can be made by an acute injection or by the slow release of any substance into the retina to correct the symptoms, treat or cure schizophrenia, psychosis, dyskinaesia, Huntington's chorea, or the symptoms of drug addiction.

According to another embodiment of the present invention there is provided a method for the treatment and/or prophylaxis of a neurological or neuropsychiatric disorder associated with altered dopamine function which comprises subjecting a patient in need of therapy which increases dopamine, by implanting foetal stem cells or retinal cells or cells from any other source onto or into the retina with the intention of facilitating the growth within the retina so that such cells might provide relief from the symptoms of Parkinson's disease or other neuropsychiatric disorders.

According to another embodiment of the present invention there is provided a method for the treatment and/or prophylaxis of side effects resulting from the prolonged treatment with an agent which treats the symptoms of Parkinson's disease by parenteral administration, wherein the agent increases dopamine. The symptoms resulting from too much dopamine include but are not limited to dyskinaesia, psychosis and exacerbation of Parkinsonian symptom, and the intraocular or intravitreal injection or administration of various agents can provide relief from the symptoms of dopamine replacement overdose.

The treatment might involve the implementation of mixing drugs for intraocular or intravitreal injection with substances such as slow release polymers that cause any drug administered via the intraocular or intravitreal route to permit the slow, sustained release of an agent into the vitreous humor over long periods of time, lasting several weeks to several months or years.

According to one embodiment of the present invention, there is provided a method for the symptomatic treatment and/or prophylaxis of a neurological or neuropsychiatric disorder associated with altered dopamine function which comprises subjecting a patient in need of therapy by administering an agent which increases dopamine, by administering dopamine precursors, dopamine agonists or any other drug that modifies dopamine function in minute volumes and doses directly into the vitreous humor of the eye by injection.

According to another embodiment of the present invention, there is provided a method for the treatment and/or prophylaxis of a neurological or neuropsychiatric disorder associated with altered dopamine function which comprises subjecting a patient in need of therapy which increases dopamine, by implanting dopamine rich cells onto or into the retina.

In another embodiment of the present invention, there is provided the use of an agent which blocks or inhibits melatonin, precursors thereof and/or metabolic products thereof in the treatment and prophylaxis of a neurological or neuropsychiatric disorder associated with altered dopamine function in need of therapy by administering an agent in minute volumes and doses directly into the vitreous humor of the eye by intraocular or intravitreal injection.

In a further embodiment of the present invention, there is provided the use of an agent which blocks or inhibits melatonin, precursors thereof and/or metabolic products thereof in the treatment and prophylaxis of a neurological or neuropsychiatric disorder associated with altered dopamine function, which comprises subjecting a patient to melatonin antagonism by implanting cells which inhibit melatonin onto or into the retina.

In another embodiment, the present invention provides a method for the preclinical diagnosis of a neurological or neuropsychiatric disorder associated with impaired dopamine function in a patient suspected of having such a disorder. For example, the method for the preclinical diagnosis may include the intraocular or intravitreal administration of a dopamine and/or a melatonin modulating agent. The method for the preclinical diagnosis may include subjecting an eye of the patient to light therapy.

Methods of early diagnosis may be employed, including methods that detect genetic or blood-borne factors, to detect neurological and/or neuropsychiatric disorders before they are symptomatically expressed (which may be several decades prior to presentation). Once the neurological and/or neuropsychiatric disorder has been detected, the method and/or use of the present invention may be employed to treat or prevent the neurological and/or neuropsychiatric disorder. In this way the treatment and/or prophylaxis of neurological and/or neuropsychiatric disorders, including Parkinson's disease, schizophrenia, dyskinaesia, Huntington's chorea and drug addiction, in accordance with the present invention may be extended.

The neurological and/or neuropsychiatric disorder associated with altered dopamine function that may be treated or prevented in accordance with various aspects of the present invention includes any neurological or neuropsychiatric disorder that may be treated or prevented by modulating neurotransmitter production in the patient. In one embodiment, the neurological and/or neuropsychiatric disorder is associated with altered dopamine, 5-hydroxytryptamine and/or noradrenalin function.

In a further embodiment, the neurological and/or neuropsychiatric disorder associated with altered dopamine function is one or more of Parkinson's disease, Huntington's chorea, periodic limb movement syndrome, restless leg syndrome, nocturnal myoclonus, Tourette's syndrome, Sundowner's syndrome, REM Sleep Behaviour Disorder, schizophrenia, Pick's disease, Punch drunk syndrome, progressive subnuclear palsy, multiple systems atrophy, corticobasilar degeneration, vascular parkinsonism, Lewy body dementias, diffuse Lewy body disease, Parkinson's plus syndrome, Korsakow's syndrome (Korsakoff's syndrome), multiple sclerosis, medication-induced motor disorders, drug-induced Parkinson's disease, neuroleptics-induced Parkinson's disease, acute dystonia, stroke-post ischemic Parkinsonism, trans-ischemic attack, akathesia dyskinaesia, tardive dyskinaesia, Alzheimer's disease, dementia, depressive pseudo dementia, hydrocephalic dementia, dementia associated with Parkinson's disease, anxiety, generalized anxiety disorder, panic disorder, agoraphobia, obsessive-compulsive disorder, post-traumatic stress disorder, acute stress disorder, depression, bipolar disorder, various personality disorders, drug addiction, drug-induced psychosis and drug withdrawal.

In another embodiment, the neurological and/or neuropsychiatric disorder associated with altered dopamine function is one or more of Parkinson's disease, Huntington's chorea, periodic limb movement syndrome, restless leg syndrome, nocturnal myoclonus, Tourette's syndrome, Sundowner's syndrome, REM Sleep Behaviour Disorder, schizophrenia, Pick's disease, Punch drunk syndrome, progressive subnuclear palsy, multiple systems atrophy, corticobasilar degeneration, vascular parkinsonism, Lewy body dementias, diffuse Lewy body disease, Parkinson's plus syndrome, Korsakow's syndrome (Korsakoff's syndrome), multiple sclerosis, medication-induced motor disorders, drug-induced Parkinson's disease, neuroleptics-induced Parkinson's disease, acute dystonia, stroke-post ischemic Parkinsonism, trans-ischemic attack, akathesia dyskinaesia or tardive dyskinaesia.

In another embodiment, the neurological and/or neuropsychiatric disorder associated with altered dopamine function is one or more of Alzheimer's disease, dementia, depressive pseudo dementia, hydrocephalic dementia, dementia associated with Parkinson's disease, anxiety, generalized anxiety disorder, panic disorder, agoraphobia, obsessive-compulsive disorder, post-traumatic stress disorder, acute stress disorder, depression, bipolar disorder and various personality disorders.

In another embodiment, the neurological and/or neuropsychiatric disorder associated with altered dopamine function is one or more of drug addiction, drug-induced psychosis and drug withdrawal.

In a further embodiment, the neurological and/or neuropsychiatric disorder associated with altered dopamine function is Parkinson's disease.

In a further embodiment, the neurological and/or neuropsychiatric disorder associated with altered dopamine function is one or more of schizophrenia, psychosis, dyskinaesia or Huntington's chorea.

The treatment or prophylaxis of a neurological and/or neuropsychiatric disorder may include the treatment or prophylaxis of the symptoms of the neurological and/or neuropsychiatric disorder. For example, with respect to Parkinson's disease, this includes the primary symptoms of Parkinson's disease including bradykinaesia or slowness, muscular rigidity and tremor (of the hands, arms, body and/or head); and the secondary symptoms of Parkinson's disease including depression, anxiety, nocturnal movement or nocturnal myoclonus, loss of balance, reduced arm swing, masked face, falling, seborrhea, bradylogia, impaired speech, excessive salivation, freezing, memory loss, bradyphrenia, irritability, mood swing, confusion, disorientation, hypersomnia, loss of appetite, dementia and insomnia.

The agent may be administered to any part of the eye. For example, the agent may be administered directly to the vitreous humor or the aqueous humor of the eye, for example by intraocular or intravitreal injection. Similarly, the agent may be administered to the outer surface of the cornea, for example through the use of opthalmic drops, and may pass through the cornea. Iontophoresis or intraocular perfusion may also be used to assist the agent to pass into the eye.

In one embodiment, the agent is administered directly to the retina, for example by intraocular injection.

In another embodiment, the agent is administered into the vitreous humor of the eye. In a further embodiment, the agent is administered into the aqueous humor of the eye. In another embodiment, the agent is administered directly into the optic nerve or optic tract.

The agent may be contained in an intraocular insert, which is inserted into the eye. In one embodiment, the intraocular insert is inserted into the vitreous humor of the eye. The term intraocular insert includes inserts produced by mixing an agent with substances such as slow release polymers that will allow the slow, sustained release of the agent into, for example, the vitreous humor over a period of time (for example several weeks, several months or years). In another embodiment, an intraocular insert may be a microchip that is able to up regulate or down regulate one or more neurotransmitters or hormones to modulate dopamine and/or melatonin production. Such neurotransmitters or hormones may include dopamine and melatonin, but could also include any neurotransmitter or hormone involved in a neurological and/or neuropsychiatric disorder, for example Parkinson's disease.

In one embodiment, the agent is administered to the eye such that it comes into contact with the retina. The term "contact" is used to denote any form of physical interaction between the agent and the retina, such that the step of contacting the agent to the retina results in modulation of neurotransmitter production in the patient.

In one embodiment, the present invention extends to the use of any agent that targets, or is suspected to target, the retina as its site of action for causing symptomatic improvement, early diagnosis, prophylaxis, treatment or prevention of Parkinson's disease or any neurological, psychiatric or neuropsychiatric disorder.

An "effective amount" of the agent is an amount sufficient to ameliorate and/or inhibit the clinical symptoms of the neurological and/or neuropsychiatric disorder. As used herein, the term "effective amount" relates to an amount of agent which, when administered according to a desired dosing regime, provides the desired therapeutic activity. Dosing may occur at intervals of minutes, hours, days, weeks, months or years or continuously over any one of these periods.

An effective amount is intended to include at least partially attaining the desired effect, or delaying the onset of, or inhibiting the progression of, or halting or reversing altogether the onset or progression of the particular condition, disease or disorder being treated, or one or more of the symptoms of the particular condition, disease or disorder being treated.

In one embodiment, the agent is administered in minute doses and volumes. In relation to agents administered, suitable dosages lie within the range of about 0.1 ng per kg of body weight to 500 mg per kg of body weight per dosage. The dosage may be in the range of 100 ng to 200 mg per kg of body weight per dosage, such as is in the range of 100 µg to 100 mg per kg of body weight per dosage. In one embodiment, the dosage may be in the range of 200 µg to 10 mg per kg of body weight per dosage. In another embodiment, the dosage may be in the range of 200 µg to 5 mg per kg of body weight per dosage. In yet another preferred embodiment, the dosage may be in the range of 200 µg to 1 mg per kg of body weight per dosage, such as 500 µg per kg body weight per dosage.

Suitable dosage amounts and dosing regimens can be determined by the attending physician and may depend on the particular condition being treated, the severity of the condition, as well as the general age, health and weight of the subject. The dosage amounts can be, administered at regular intervals, or by methods which provide sustained release over a long period of time, for example days, months, years.

Advantageously, the amount of agent required to produce the desired therapeutic activity is much smaller when the agent is administered to the eye than if the agent is administered systemically by another route. Accordingly, as very small doses of therapeutic agents can be administered in very small volumes to achieve therapeutic relief from neurological and/or neuropsychiatric disorders, potential side effects arising from the administration of the agent may be reduced.

The agent may be administered in a single dose or a series of doses. If the agent is a compound, while it is possible for the compound to be administered alone it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The agent may also be administered using a method that facilitates access to the retina; for example using penetration enhancers or physical means, such as sonic vibration.

The carrier must be pharmaceutically "acceptable" in the sense of being compatible with the other ingredients of the composition and not injurious to the subject. Compositions include those suitable for administration to the eye, including into the eye by intravitreal or intraocular injection, and to the cornea of the eye using ophthalmic drops. Compositions suitable for administration for iontophoresis and intraocular perfusion may also be used. The compositions may conveniently be presented in unit dosage form and may be prepared by any methods well known in the art of pharmacy. Such methods include the step of bringing into association the agent with the carrier which constitutes one or more accessory ingredients. In general, the compositions are prepared by uniformly and intimately bringing into association the agent with liquid carriers or finely divided solid carriers or both, and then if necessary shaping the product.

An agent or agents for intraocular or intravitreal injection may be administered in the form of a composition, together with one or more pharmaceutically acceptable carriers, dilatants, adjuvant and/or excipients.

A composition of the agent to be used in the present invention for intraocular or intravitreal injection may be presented as discrete units such as capsules, sachets or small tablets each containing a predetermined amount of the agent; as a powder or granules as a solution or suspension in aqueous or non-aqueous liquid; or as an oil-in-water emulsion or a water-in-oil liquid emulsion. The agent may be presented as a slow-release pellet, bolus, electuary or paste. The agent may be formulated for topical application to they eyes or instillation into the space between the eyeball and eyelids. The agent may also be formulated for subconjunctival injection.

The composition may be formulated as a bolus, electuary, paste, solution, suspension, ointment and slow-release preparation (including pellets). Additives, such as buffers, stabilizers, preservatives and thickening agents may also be included. Preservatives may include bactericidal and fungicidal agents, such as phenyl mercuric acetate or nitrate, benzalkonium chloride, thimerosal, chlorobutanol or chlorohexidine. Thickening agents may include hypromellose. Buffering agents may include citrate, borate or phosphate salts. Stabilisers may include glycerin and polysorbate 80.

It should be understood that in addition to the ingredients particularly mentioned above, the composition of agents for use in this invention may include other agents conventional in the art having regard to the type of composition in question. In one embodiment, if the composition is to be administered to the cornea, it may be isotonic with the lacrimal fluid and have an equivalent pH (in the range of pH 6-8).

If the agent is to be administered in an opthalmic ointment, the ointment may comprise a white petrolatum-mineral oil base, which may include anhydrous lanolin, or a polyethylene-gelled mineral oil base.

The amount of agent in the composition will vary according with the disorder to be treated or prevented, and the manner in which the agent is to be administered. In one embodiment, the amount of agent will be from 0.001-10% wt/vol of active ingredient per individual application dose, preferably from 0.0025-7% wt/vol; and most preferably from 0.005-7% wt/vol.

Regardless of the type of composition, the composition should not interfere with vision and not cause irritation.

The agent may also be formulated as depot preparations. Such long acting formulations may be administered by implantation into any part of the eye, including the vitreous humor and the sclera, to provide release into the vitreous humor. Thus, the agent may be formulated with suitable polymeric or hydrophobic materials (as an emulsion in an acceptable oil or ion exchange resin), or sparingly soluble derivatives, for example as a sparingly soluble salt. Preferably, the agent is administered in the form of a polymeric implant, such as, a micro sphere adapted for sustained or pulsatile release where dopamine and/or melatonin and/or any transmitter, hormone or neuromodulators has been altered, or is thought to be altered in the retina or in the brain in any neurological, psychiatric or neuropsychiatric disease or disorder.

As used herein, the term "agent" includes any substance of material form that modulates neurotransmitter production. This may include a cell, virus, protein or small molecule that modulates neurotransmitter production. Accordingly, the term "agent" does not include incorporeal substances, such as light.

In one embodiment, the agent is a cell. The cell may be a genetically modified cell or virus that modulates neurotransmitter production. This especially includes a genetically modified cell or virus that modulates dopamine and/or melatonin production, including those that alter other neurotransmitters, such as serotonin, noradrenalin and GABA. The agent may also be a stem cell, including a dopamine and/or melatonin modulating stem cell, a retinal cell, a dopamine rich cell or a cell that inhibits or blocks melatonin.

In another embodiment, the agent blocks and/or inhibits melatonin production or action. The agent may also block and/or inhibit melatonin, precursors thereof and/or metabolic products thereof. The agent may be a melatonin antagonist, a beta adrenergic antagonist (such as propranolol or atenolol), a calcium channel blocker or melanocyte stimulating hormone (MSH). The melatonin antagonist may be a melatonin analogue or metabolite or any other indolamine, neurotransmitter, neuromodulator, neurohormone or neuropeptide that has an affinity for the melatonin receptor.

The agent may stimulate dopamine production, precursors of dopamine and/or metabolic products of dopamine, including dopamine, L-dopa, bromocriptine, pergolide, Stalevo® or Cabaser®.

In one embodiment, the agent is a compound of formula (I)

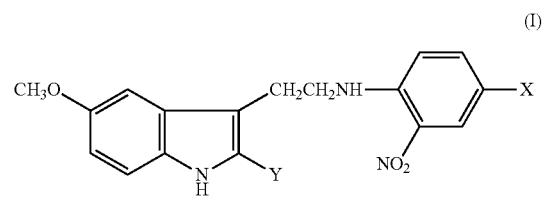

where X is $NO_2$ or $—N_3$ and Y is H or I. Such compounds include ML-23.

In another embodiment, the agent is a compound of formula (II)

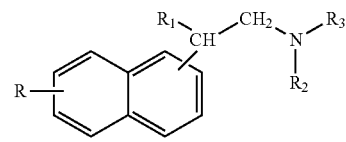

wherein

R represents a hydrogen atom or a group $—O—R_4$ in which $R_4$ denotes a hydrogen atom or a substituted or unsubstituted group chosen from alkyl, cycloalkyl, cycloalkylalkyl, phenyl, phenylalkyl and diphenylalkyl, $R_1$ represents a hydrogen atom or a group $—CO—O—R_5$ in which $R_5$ denotes a hydrogen atom or a substituted or unsubstituted alkyl group, $R_2$ represents a hydrogen atom or a group $—R'_2$ with $R'_2$ representing an alkyl or substituted alkyl radical, $R_3$ represents

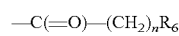

in which n represents 0 or an integer from 1 to 3 and $R_6$ represents a hydrogen atom or an alkyl, substituted alkyl, alkene, substituted alkene, cycloalkyl or substituted cycloalkyl group, or a substituted or unsubstituted heterocyclic group chosen from pyrrolidine, piperidine, piperazine, homopiperidine, homopiperazine, morpholine and thiomorpholine;

in which X represents an oxygen or sulfur atom, n' represents 0 or an integer from 1 to 3 and $R_7$ represents an alkyl, substituted alkyl, cycloalkyl, substituted cycloalkyl, phenyl or substituted phenyl group, with the proviso that if:

R represents an alkoxy group,

R represents a hydrogen atom and $R_3$ represents a group —CO—$R_8$ in which $R_8$ represents a hydrogen atom, a methyl group or a methyl or propyl group substituted with a halogen, or if $R_3$ represents a group —C(=X)—NH—$(CH_2)_{n'}$—R, in which X, n' and $R_7$ are as defined above, then $R_1$ cannot be a hydrogen atom, their optical isomers and their addition salts.

Other suitable agents include those described in WO02/28347 in the name of Neurim Pharmaceuticals (1991) Ltd, the entire contents, of which is incorporated herein by reference.

The agent may be an antioxidant, such as melatonin, vitamin A, C or D, alpha-tocopherol or selenium. The agent may be a protein, such an antibody.

The agent may reduce dopamine production, or block dopamine receptors. The agent may be haloperidol, thioxanthene, fluphenazine, lithium carbonate, thioidazine, valium, diazepam, pimozide, chlorpromazine, benzodiazepines, respiradol or quetiapine fumarate.

The agent may be one or more of domperidone, haloperidol, pimozide, clonazipine, sulperide, metaclopromide, ML-23, spiroperidol, haloperidol, thioxanthene, fluphenazine, lithium carbonate, thioidazine, valium, diazepam, pimozide, chlorpromazine, benzodiazepines, respiradol, quetiapine fumarate, propranolol, atenolol, melanocyte stimulating hormone (MSH), selegiline, parlodel, cogentin, Kripton, cabaser, benztropine, biperiden HCl, apomorphine, entacapone, pergolide, amantadine, L-dopa, tetrabenazine, resagaline and carbidopa, pharmaceutically acceptable salts thereof, derivatives thereof and/or prodrugs thereof.

Different agents act on the dopamine or melatonin pathways (directly or indirectly) in different ways. For example, in the treatment of Parkinson's disease a decrease in melatonin and an increase in dopamine is desired. Suitable agents include, but are not limited to, the following:

Dopamine Agonists

L-dopa, levo dopa/carbo dopa, Dopamine, Deprenyl, Adrenaline, Noradrenaline, Tyrosine, Benztropine, amantadine, Bromohexol, Apomorphine and Biperiden.

Catichol O-Methyl Transferase Inhibitors

Comtan.

Monoamine Oxidase Inhibitors

Pargyline, Tranylcyptomine, Nialamide, Phenylzine. Isocarcoxizide, Iproniazide. Selegaline and Resegaline.

Anticholinergics

Atropine and Akineton.

Melatonin Antagonists

Luzindole, S-20928, Prazosin, DH-97, ML-23, cis-4-phenyl-2-propionamidotetralin (4-P-PDOT), N-(substituted-anilinoethyl)amides for melatonin azido- and isothiocyanato-substituted indoles melatonin analogues where the 5-methoxyl and 3-amidoethyl side chains act as the functional components see also WO02/28347.

Other Dopamine Agonists

Bromocryptine, Amantadine, Cabergoline and Pergolide.

For treating depression and the depression associated with Parkinson's disease, it is also desirable to decrease melatonin and increase dopamine. Suitable agents include, but are not limited to, Fluoxetine, Fluvoxamine, Paroxetine, Sertraline, Citalopram, imipramine, amityiptaline, desmehtylimipramine, comipramine, Mirtazapine and Trazodon. The melatonin antagonists described above may also be suitable.

For treating Dyskinaesia or Drug-induced psychosis and related addiction and withdrawal the following agents may be suitable.

Naloxone, Methadone, Disuifram, Nicotine, Buprenorphine, Naltrexone, Buprorion, Metaelopromide, Flumazenil, Atropine sulfate, oxytocin and other hormones such as the gonadals.

Antipsychotics may also be suitable for treating Dyskinaesia or Drug-induced psychosis. Examples include but are not limited to:

Phenothyazines

Chlorpromazine, Fluphenazine, Trifluperizine, Thioridazine and Lithium

Butyrophenones

Haloperidol, Flupenthixol, Clopenthixol and pimozide.

Atypical Neuroleptics

Benzamide, Sulpiride, Pimozide, Remoxipride, Dibenzodiazepine, Clozapine, olanzapine, Sertindole, Risperidone, Quetiapine, Imipramine, Clomipramine.

Benzodiazepines

Diazepam, Clonazepam Clobazam, Spiperone, Sulperide and Domperidone.

The agent may be used to treat or prevent any neurological and/or neuropsychiatric disorder associated with altered dopamine function, by preventing or treating the degeneration of neurotransmitters such as melatonin, dopamine, noradrenalin, glutamate, or any oxidative process or substance thought to be responsible for the disorder.

The modulation of neurotransmitter production in the patient includes any effect on neurotransmitter production in the patient, especially in the retinal hypothalamic tract. In one embodiment, administration of the agent results in modulation of melatonin production in the pineal gland.

The agent may modulate the production of one or more neurotransmitters selected from acetylcholine, GABA, serotonin, dopamine, noradrenalin and melatonin, precursors thereof and/or metabolic products thereof. In one embodiment, the neurotransmitters are dopamine or melatonin, precursors thereof and/or metabolic products thereof.

In one embodiment, modulation of neurotransmitter production is an increase in dopamine production, precursors thereof and/or metabolic products thereof. In another embodiment, modulation of neurotransmitter production is an inhibition of melatonin production, precursors thereof and/or metabolic products thereof. It is believed that the step of modulating neurotransmitter production allows the neurological and/or neuropsychiatric disorder to be treated or prevented.

The patient may be a human or an animal such as a domestic or wild animal, particularly in animals of domestic importance.

In another embodiment, one or more further agents are administered sequentially, separately or simultaneously with the agent outlined above. The one or more further agents may be administered parenterally. In another embodiment, the one or more further agents are administered to the eye.

The one or more further agents may be an agent used in the treatment of neurological or neuropsychiatric disorders, such as, for example, domperidone, haloperidol, pimozide, clonazipine, sulperide, metaclopromide, ML-23, spiroperidol or another drug which modulates normal dopamine or melatonin transmission. The one or more further agents may be one of the agents discussed above.

The one or more further agents may be administered by any systemic route, including by intraocular or intravitreal injection.

In a further embodiment, the eye of the patient is subjected to light therapy sequentially, separately or simultaneously with the administration of the agent.

It has been found that pulsing or flashing light increases dopamine in the retina. In a further embodiment, there is provided a method for the treatment and/or prophylaxis of a neurological and/or neuropsychiatric disorder comprising the step of subjecting an eye of a patient to pulsing light therapy such that the patient's eye is exposed to light for a time and under conditions sufficient to modulate neurotransmitter production in the patient. In one embodiment of this method, the pulsing or flashing light is applied from one pulse per second to one pulse per 20 minutes, with a duration of from 1 second to 20 minutes. The intensity may be, for example, up to 20,000 lux. Broad spectrum white light may be used, although blue and green spectrum may also be used. The light therapy is applied to the eyes while open, generally though the use of a suitable light box on other light emitting device.

The administration of the one or more further agents may involve combination therapies where an agent is administered to the patient, for example by intraocular or intravitreal injection, which increases dopamine function in the retina, and at the same time administering to the patient intraocular or intravitreal injections of an agent that has other effects, such as decreasing melatonin function in the retina. The possible numbers and types of drugs that can be employed in this capacity will be appreciated by those skilled in the art.

The administration of the one or more further agents may involve combination therapies where an agent is administered to the patient, for example by intraocular or intravitreal injection, which for example increases dopamine function in the retina, and at the same time topically administering agents onto the corneal surface of the eye of the patient.

The administration of the one or more further agents may involve combination therapies where an agent is administered to the patient, for example by intraocular or intravitreal injection, which for example increases dopamine function in the retina, and at the same time administering to the patient agents that increase dopamine function by any other suitable route of administration including, for example, oral, implantation, rectal, inhalation, insufflation (mouth or nose), topical (including buccal and sublinguinal), vaginal and parenteral (including subcutaneous, intramuscular, intravenous, intrasternal and intradermal) administration.

The administration of the one or more further agents may involve combination therapies where an agent is administered to the patient, for example by intraocular or intravitreal injection, which for example increases dopamine function in the retina, and at the same time subjecting the patient to brain lesions of the globus pallidus or to electrical stimulation of the thalamus, globus pallidus, the subthalamic nucleus or other parts of the nigro-striatal dopamine system that are routinely employed the treatment of Parkinson's disease or other neuropsychiatric disorders.

The administration of the one or more further agents may involve combination therapies where foetal cells of various kinds or stem cells are implanted into the retina of the patient, which for example increases dopamine function in the retina, and at the same time subjecting the patient to brain lesions of the globus pallidus or to electrical stimulation of the thalamus, globus pallidus, the subthalamic nucleus or other parts of the nigro-striatal dopamine system that are routinely employed the treatment of Parkinson's disease or other neuropsychiatric disorders.

The administration of the one or more further agents may involve combination therapies where an agent is administered to the patient, for example by intraocular or intravitreal injection, which for example increases dopamine function in the retina, and at the same time subjecting an eye of the patient to light therapy.

The administration of the second agent may involve combination therapies where an agent is administered to the patient, for example by intraocular or intravitreal injection, which for example decreases dopamine function in the retina, and at the same time subjecting an eye of the patient to light therapy.

The present invention may involve combination therapies comprising the administration of an agent to the patient, for example by intraocular or intravitreal injection, which increases dopamine function in the retina; and simultaneously administering any combination of therapeutic drugs for systemic administration, for example melatonin antagonists and dopamine replacement; and at the same time subjecting an eye of the patient to light therapy.

The present invention may also involve combination therapies comprising the administration of an agent to the patient, for example by intraocular or intravitreal injection, which decreases dopamine function in the retina, and simultaneously administering any combination of therapeutic drugs for systemic administration, for example melatonin antagonists and dopamine replacement, and at the same time subjecting an eye of the patient to light therapy.

The present invention may also include the topical application of a substance to the eye to dilate the pupil while introducing another substance by intravitreal injection and/or exposing the patient to light for the purpose of preventing, treating or slowing the progression of Parkinson's disease or other neuropsychiatric disorder.

In one embodiment, an agent may be administered to a patient for the treatment and/or prophylaxis of a neurological and/or neuropsychiatric disorder, and a second agent may be administered to the patient, including but not limited to an agent or cell implant, to symptomatically improve visual function.

In another embodiment, the agent may be administered at a predetermined time or over a predetermined period which would induce a transient form of the neurological and/or neuropsychiatric disorder or change the chemistry of the vitreous humor or fluid adjacent to the retina or blood levels of various hormones. The use of light therapy on its own or in combination with such injections would also induce a transient form of the disease or change retinal cerebral spinal fluid or circulating levels of melatonin or other hormonal or fluid borne indices of the disease that would be detectable using assay procedure and thereby permit early detection of the disease.

Certain embodiments of the invention will now be described with reference to the following examples which are intended for the purpose of illustration only and are not intended to limit the scope of the generality hereinbefore described.

EXAMPLES

Example 1

When lesions are strategically placed in the nigro-striatal dopamine system in the brains of experimental animals then Parkinsonian symptoms including bradykinaesia, tremor and rigidity and loss of vegetative function are seen. When a similar loss of dopamine occurs to that in humans, as detected by post-mortem examination, then Parkinson's disease results (Hornykiewicz, O. Biochem. Pharmacol., 24, 1061, 1975).

At appropriate concentrations, the neurotoxin 6-hydroxy dopamine produces specific and permanent depletion of dopamine in the brain and more specifically of the nigro-striatal dopamine system (Ungerstedt, U. et al, Adv. Neurol., 5, 421, 1974; Willis, G. L. & Armstrong, S. A., Brain Res. Rev., 27, 177, 1998). Intracranial injections of 6-hydroxy dopamine were used to produce a model of Parkinson's disease (and schizophrenia). Bilateral lesions produced a vegetative, akinetic syndrome in which there is a lack of voluntary movement, hunched posture and body weight loss accompanied by a loss in the ability to eat and drink.

a) After preparatory surgery that permitted access to the brain, rats were induced with experimental Parkinson's disease by injection of the neurotoxin 6-hydroxy dopamine into the nigro-striatal dopamine system. Enucleation of an eye was then performed on the same side (PD+Ipsi) or the opposite side (PD+Contra) to which Parkinson's disease was produced. Parkinson's disease was also produced on one side only without enucleation (PD) and these are compared to normal rats without Parkinson's disease or enucleation (Control).

The effect of enucleation on horizontal movement and on the ability to retract a limb, respectively, in rats with experimental Parkinson's disease was then tested (see FIGS. 1, 2, 10, 11, 12 and 13). Those animals with Parkinson's disease only (PD) were not as severely Parkinsonian as were those with Parkinson's disease plus ipsilateral enucleation (PD+Ipsi). This indicates that the eye is important in the development of neuropsychiatric disorders such as Parkinson's disease (PD).

b) After preparatory surgery that permitted access to the brain, rats were induced with bilateral experimental Parkinson's disease by injection of the neurotoxin 6-hydroxy dopamine into the nigro-striatal dopamine system. On days 2, 3 and 4 after surgery a single 2 µl intraocular or intravitreal injection was made into the vitreous humor of both eyes. The solution injected was either a 10 mMol solution of ML-23 (PD+IODrug) or a 10 mMol solution of vehicle (PD+IOVeh). The vehicle used was 70% DMSO. For comparison, a control group was not made Parkinsonian but received intraocular or intravitreal injection of vehicle in the same volume as the experimental groups (C+IOVeh).

Figure 2:
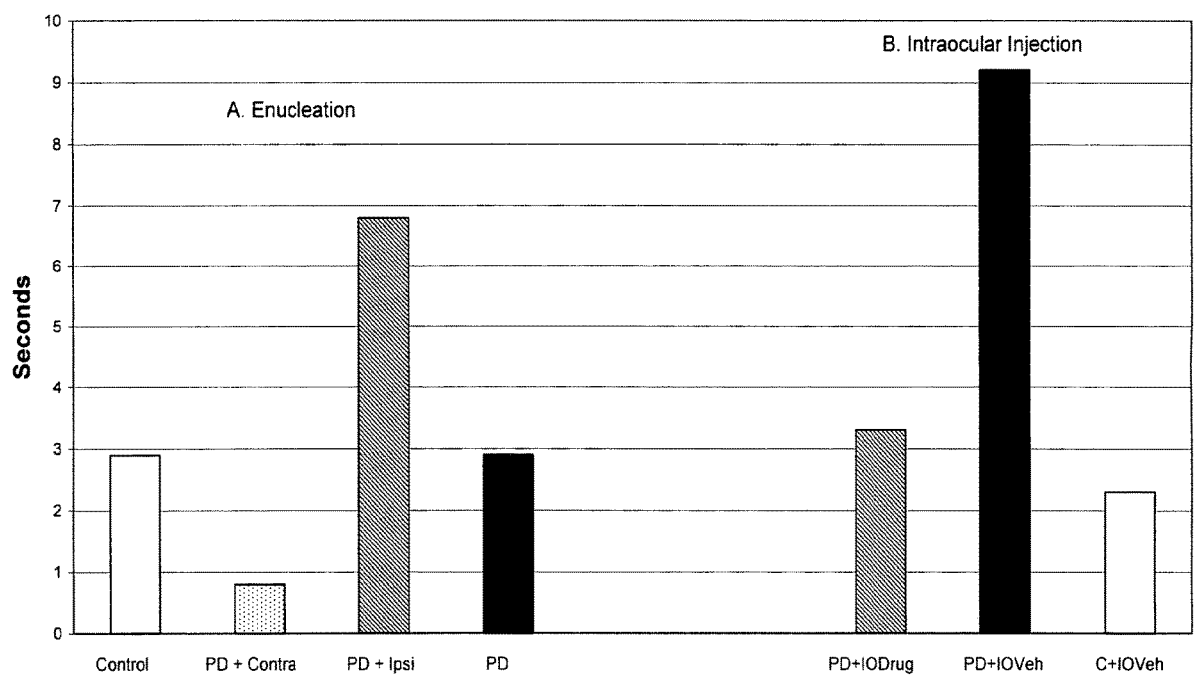
FIG. 2 is a graph showing the effect of enucleation or surgical removal of the eye of a rat, as depicted by the effect on horizontal movement in experimental Parkinson's disease (A), and the effect of bilateral, intraocular or intravitreal injection of ML-23 on the ability of a rat with experimental Parkinson's disease to retract its front limb (B).
Figure 3:
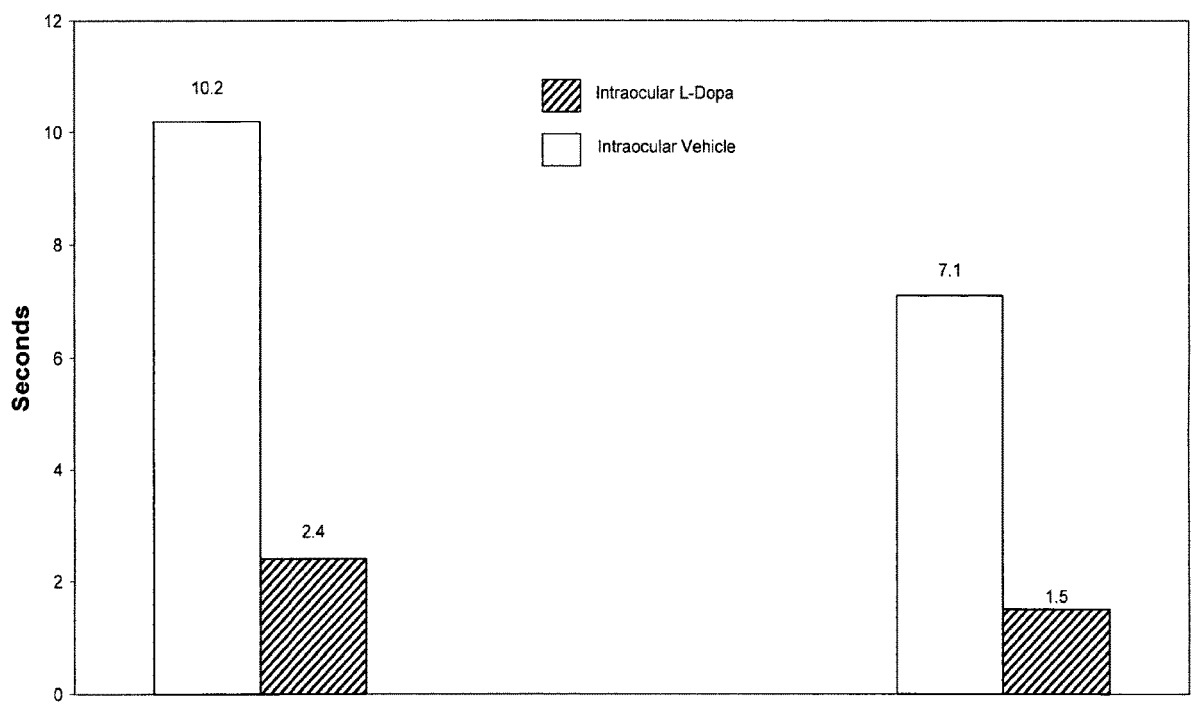
FIG. 3 is a graph showing the effect of bilateral, intraocular or intravitreal injection of the anti-Parkinsonian drug L-dopa on the horizontal movement of a rat with experimental Parkinson's disease.

The effect of these intraocular or intravitreal injections on horizontal movement and on the ability to retract a limb, respectively, in rats with experimental Parkinson's disease were then tested (FIGS. 1 and 2). Those animals receiving intraocular or intravitreal injection of an anti-Parkinsonian drug (PD+IODrug) showed better horizontal movement and better performance on the ability to move the front limb than did Parkinsonian animals injected with vehicle (PD+IOVeh). Other anti-Parkinsonian drugs produced a similar effect. This indicates that therapeutic intervention at the level of the eye may be useful for treating Parkinson's disease in humans.

c) After preparatory surgery that permitted access to the brain, rats were induced with bilateral experimental Parkinson's disease by injection of the neurotoxin 6-hydroxy dopamine into the nigro-striatal dopamine system. On days 5, 6, 12 and 16 after surgery a single 2 µl intraocular or intravitreal injection was made into the vitreous humor of both eyes. The solution was either a 100 mMol solution of L-dopa (Intraocular L-Dopa) or a 100 mMol solution of vehicle (Intraocular Vehicle).

The effects of these intraocular or intravitreal injections on the ability to ambulate and on the ability to retract a limb, respectively, in rats with experimental Parkinson's disease were then tested. (The results are shown in FIGS. 3, 5, 6, 7, 8 and 9). The bars to the left on the graph of FIG. 3 relate to the latency to retract a limb and the bars on the right relate to the latency to ambulate. Other anti-Parkinsonian drugs and treatments would be expected to produce a similar effect. This indicates that therapeutic intervention at the level of the eye using routine anti-Parkinsonian medicaments, (i.e. L-Dopa) may also be useful for treating the Parkinson's disease.

Example 2

Lesions to the brain dopamine systems in mammalian brain serve as models for various neuropsychiatric disorders. When drugs such as amphetamines are administered to animals for a certain period of time psychotic symptoms develop such as increased activity, agitation and decreased latency time to perform various motor tasks. In other words, opposite to those symptoms seen in Parkinson's disease, the time to perform various motor tasks decreased: they perform them quicker.

At appropriate concentrations, the addictive drug, dl-amphetamine (1 mg/kg) was injected intraperitoneally to produce psychosis and addiction in Sprague-Dawley rats. After 5 days of such treatment each animal was tested for their level of activity in a computerized activity chamber and on three motor tests. On the day after completion of the injections half the animals received a 2 µl injection of haloperidol (12.5 µg/µl) into the vitreous humor, just in front of the retina. The other half of the animals received a 2 µl injection of vehicle (80% DMSO solution) into the vitreous humor. The effects of such injections on various parameters of movement, such as the latency to ambulate and the latency to retract a front paw, were measured three hours after animals received their intravitreal injection.

Figure 4:
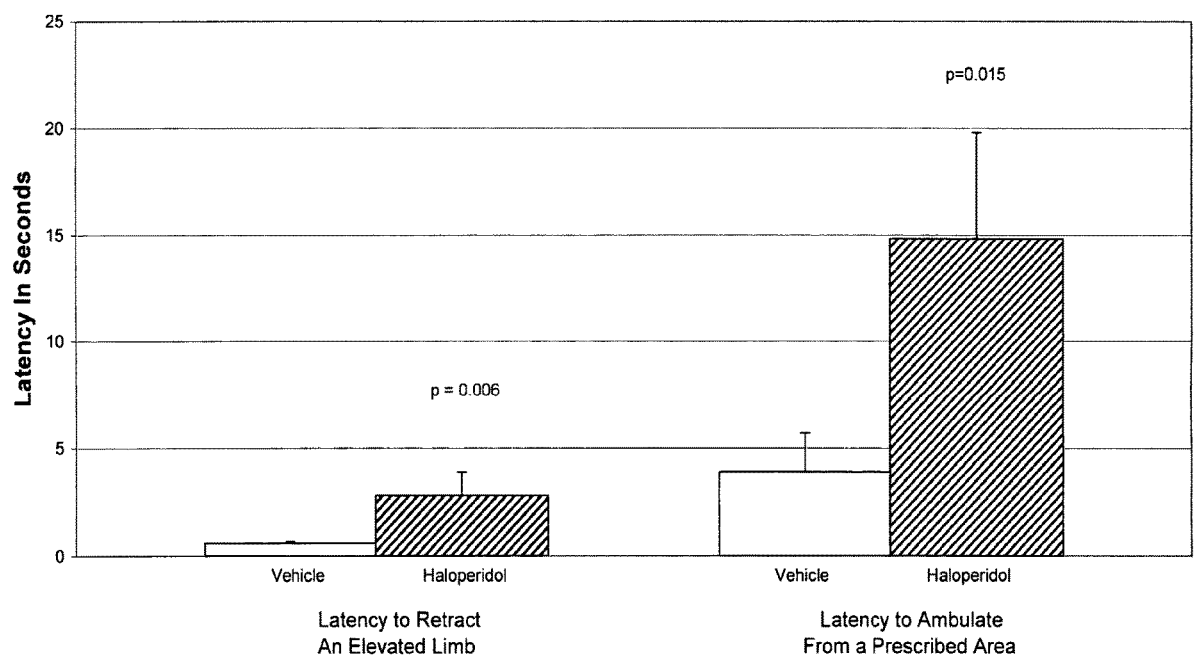
FIG. 4 is a graph showing the effect of bilateral, intraocular or intravitreal injection of 2 μl of 12.5 μg/μl haloperidol into rats that had been pre-tested for 5 days prior with 1 mg/kg of dl-amphetamine.
Figure 5:
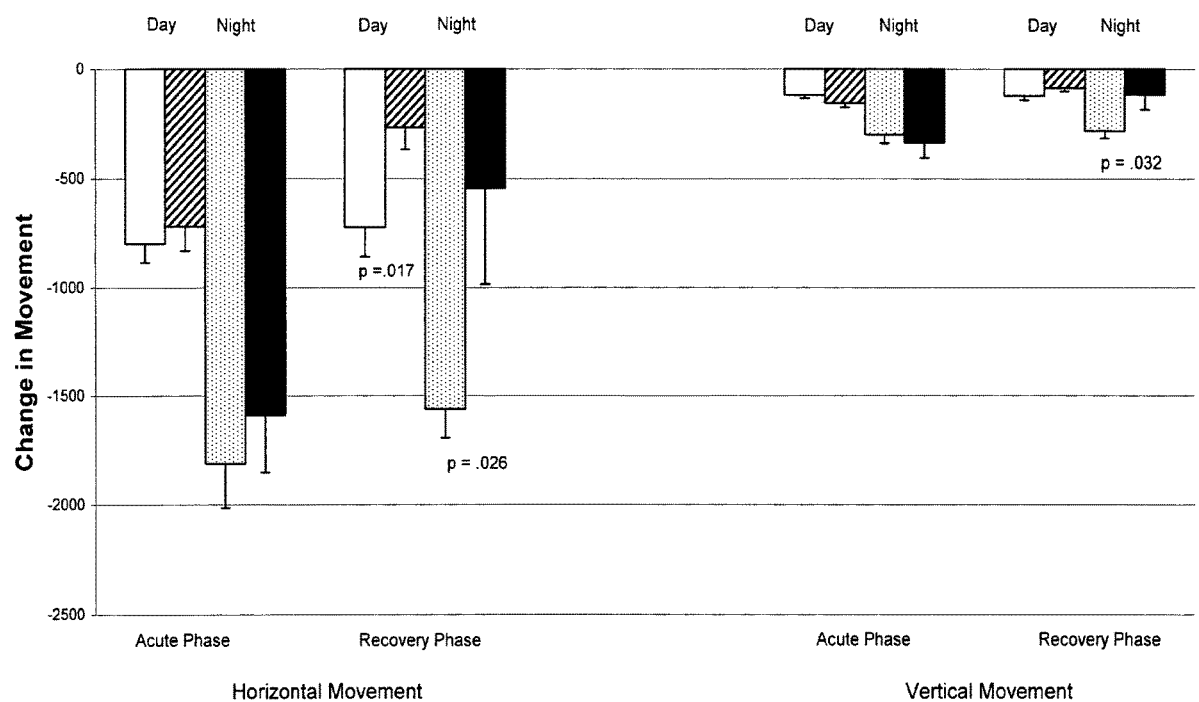
FIG. 5 is a graph showing the effect of intravitreal injection of L-dopa on vertical or horizontal movement in rats with experimental Parkinson's disease, during the day and night.
Figure 6:
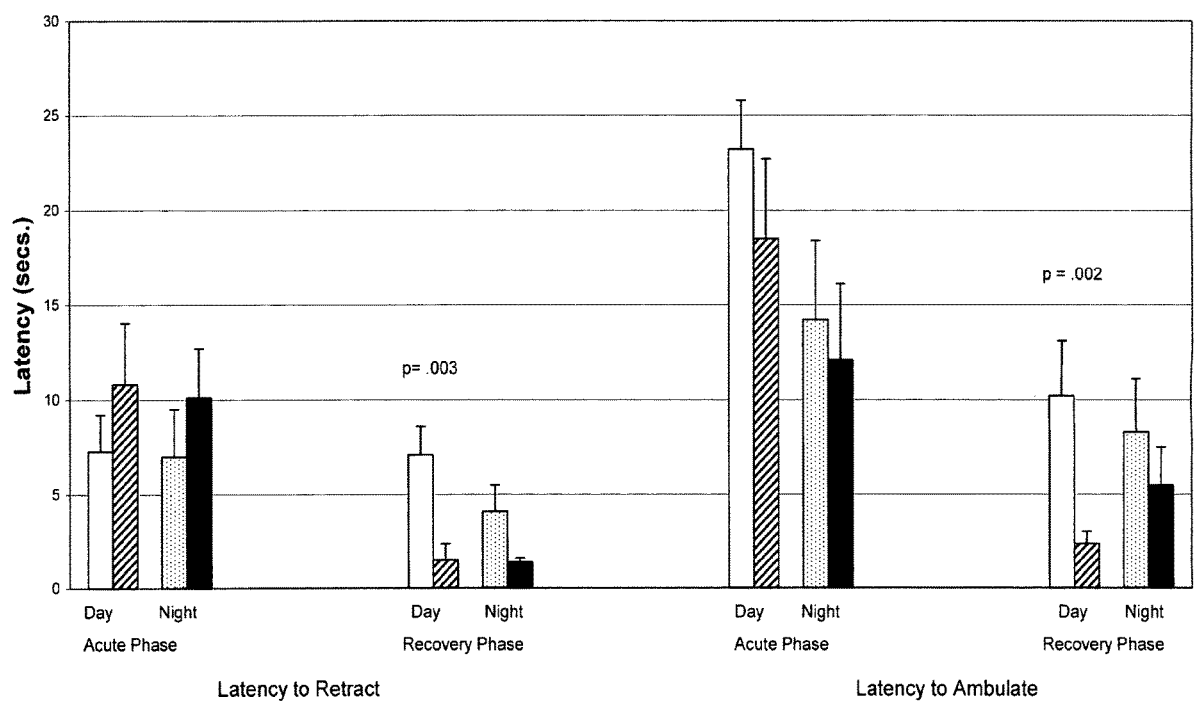
FIG. 6 is a graph showing the effect of intravitreal injection of L-dopa on retraction and ambulation in rats with experimental Parkinson's disease, during the day and night.
Figure 7:
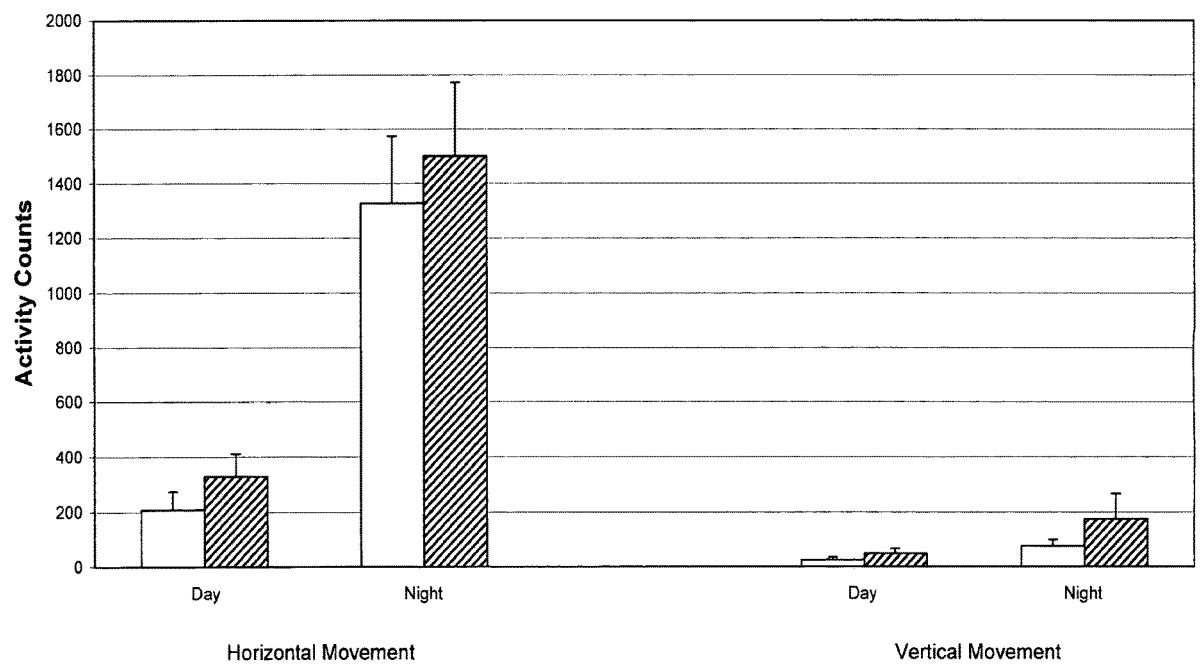
FIG. 7 is a graph showing the residual effects (at least 48 hrs after withdrawal of agent) of intravitreal injection of L-dopa on horizontal and vertical movement in rats with experimental Parkinson's disease, during the day and night.
Figure 8:
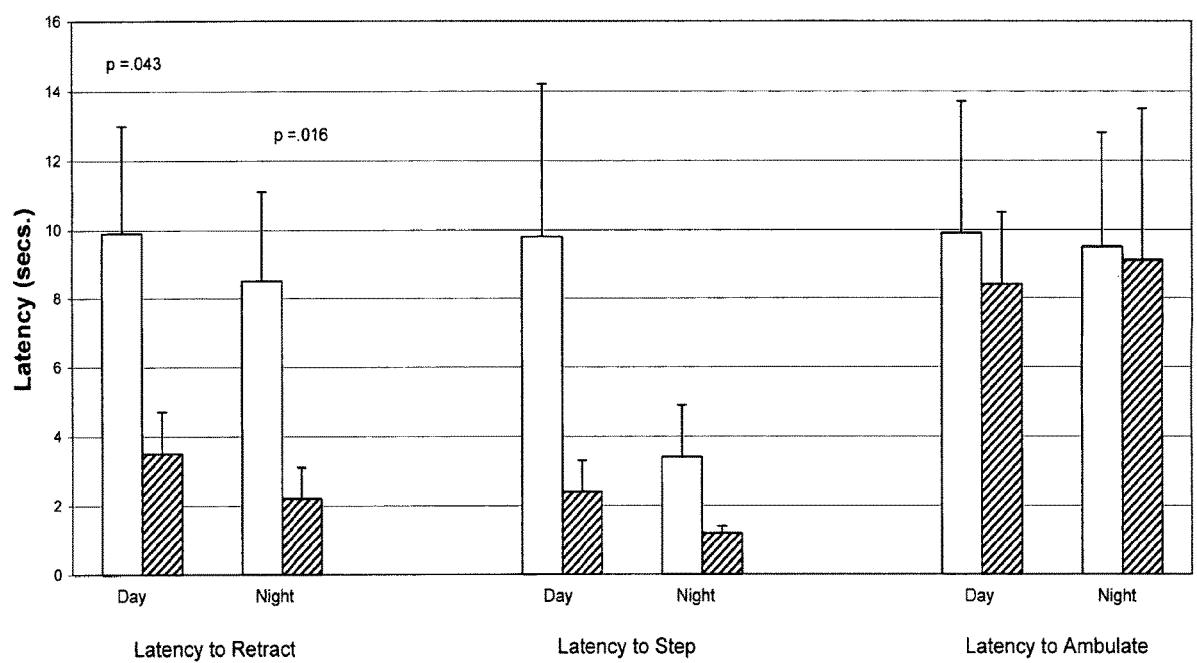
FIG. 8 is a graph showing the residual effect (at least 48 hrs after withdrawal of agent) of intravitreal injections on the latency to retract, step and ambulate in rats with experimental Parkinson's disease, during the day and night.
Figure 9:
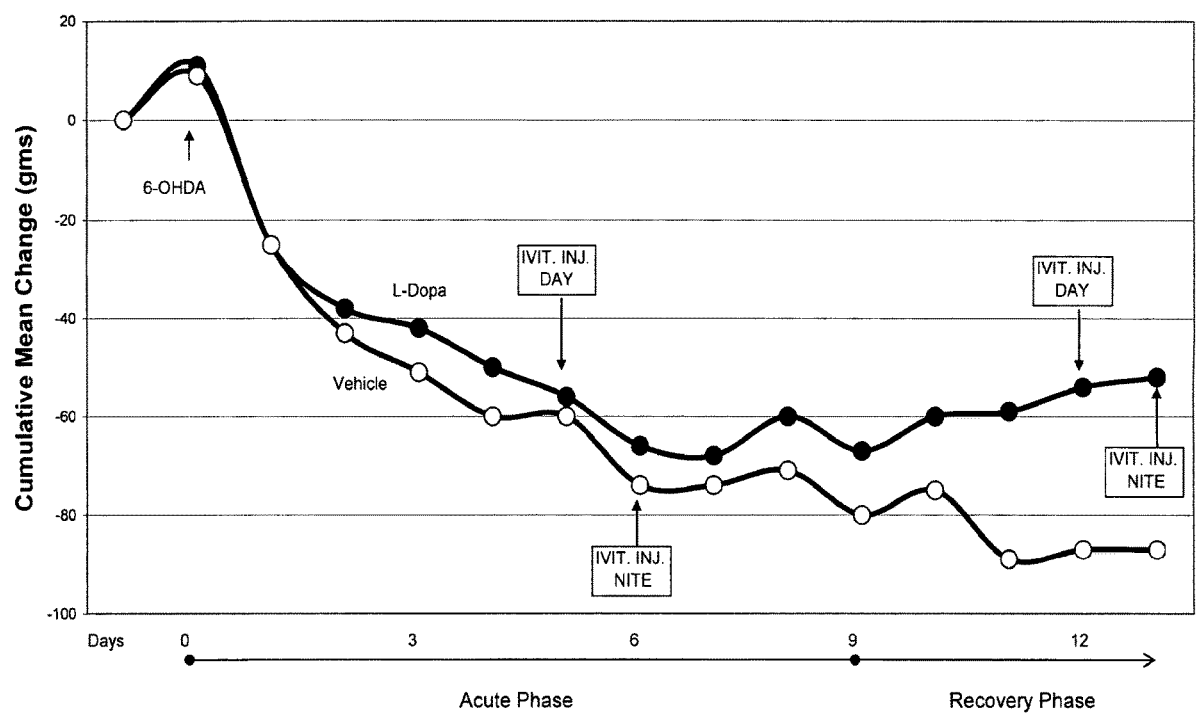
FIG. 9 is a graph showing the effect of intravitreal injection of L-dopa on body weight in rats with experimental Parkinson's disease, during the day and night.
Figure 10:
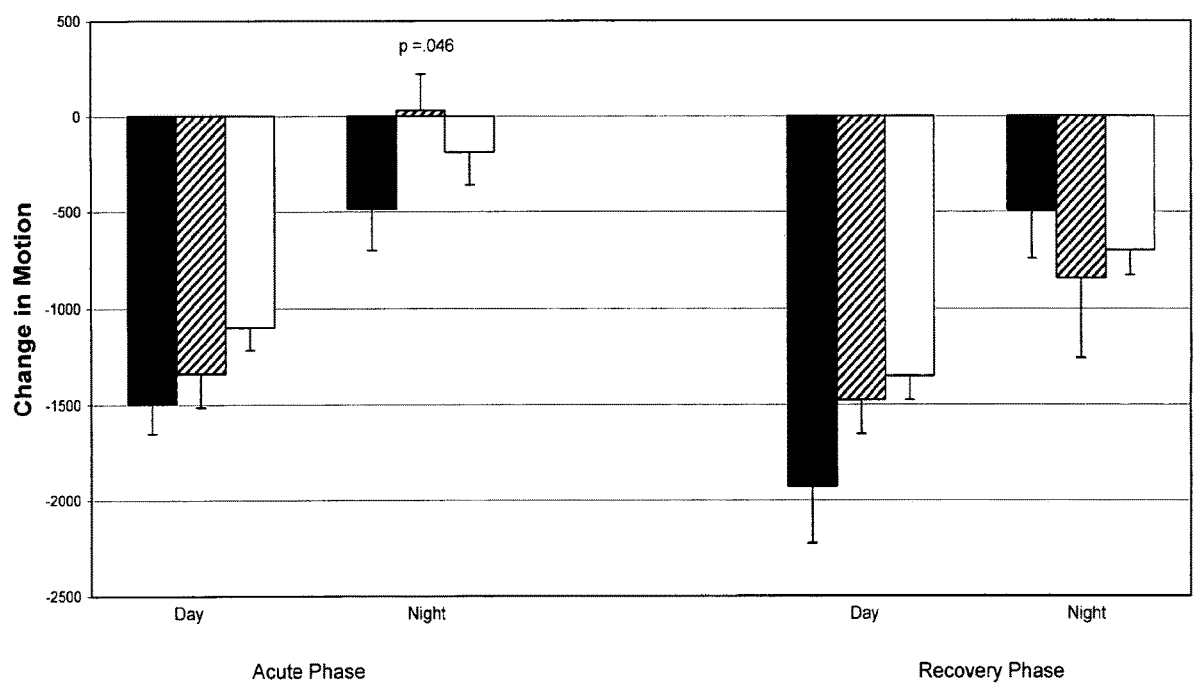
FIG. 10 is a graph showing the effect of intravitreal injection of ML-23 on horizontal movement in rats with experimental Parkinson's disease, during the day and night.
Figure 11:
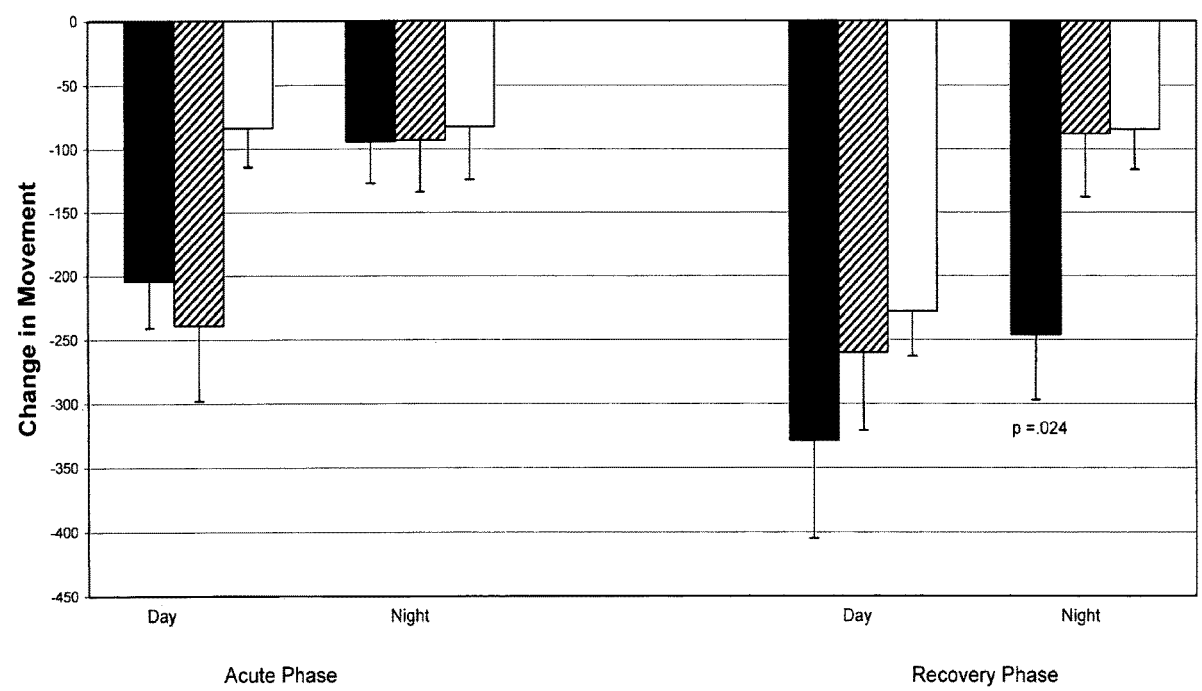
FIG. 11 is a graph showing the effect of intravitreal injection of ML-23 on vertical movement in rats with experimental Parkinson's disease during the day and night.
Figure 12:
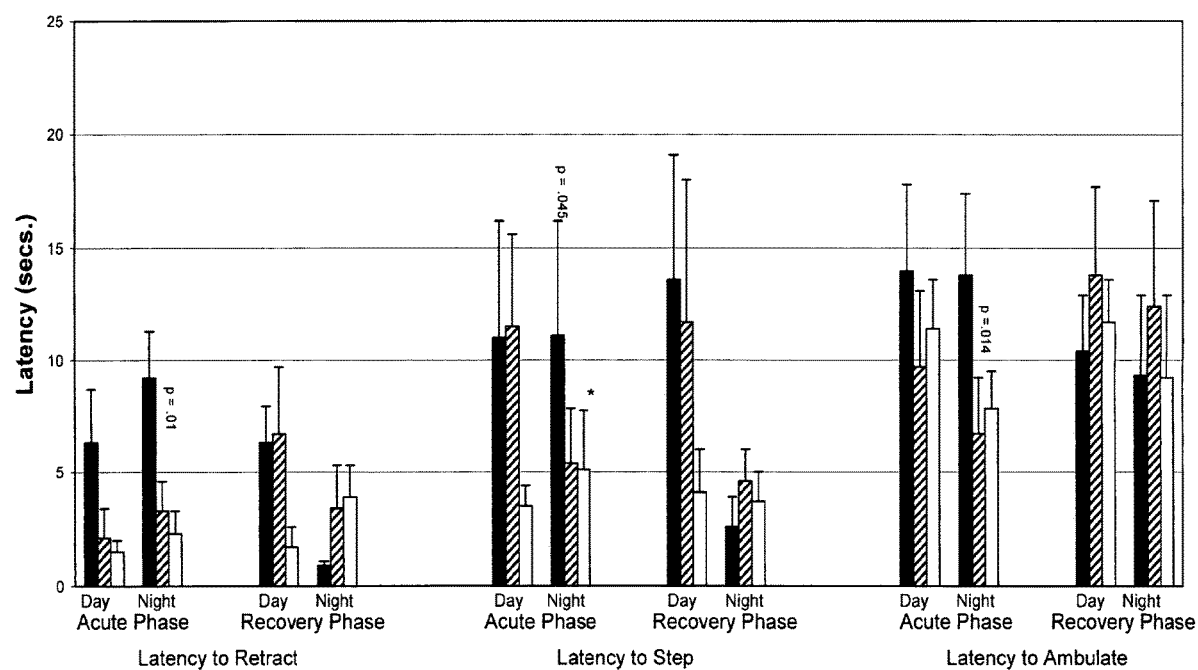
FIG. 12 is a graph showing the effect of intravitreal injection of ML-23 on latency to retract, step and ambulate in rats with experimental Parkinson's disease during the day and night.
Figure 13:
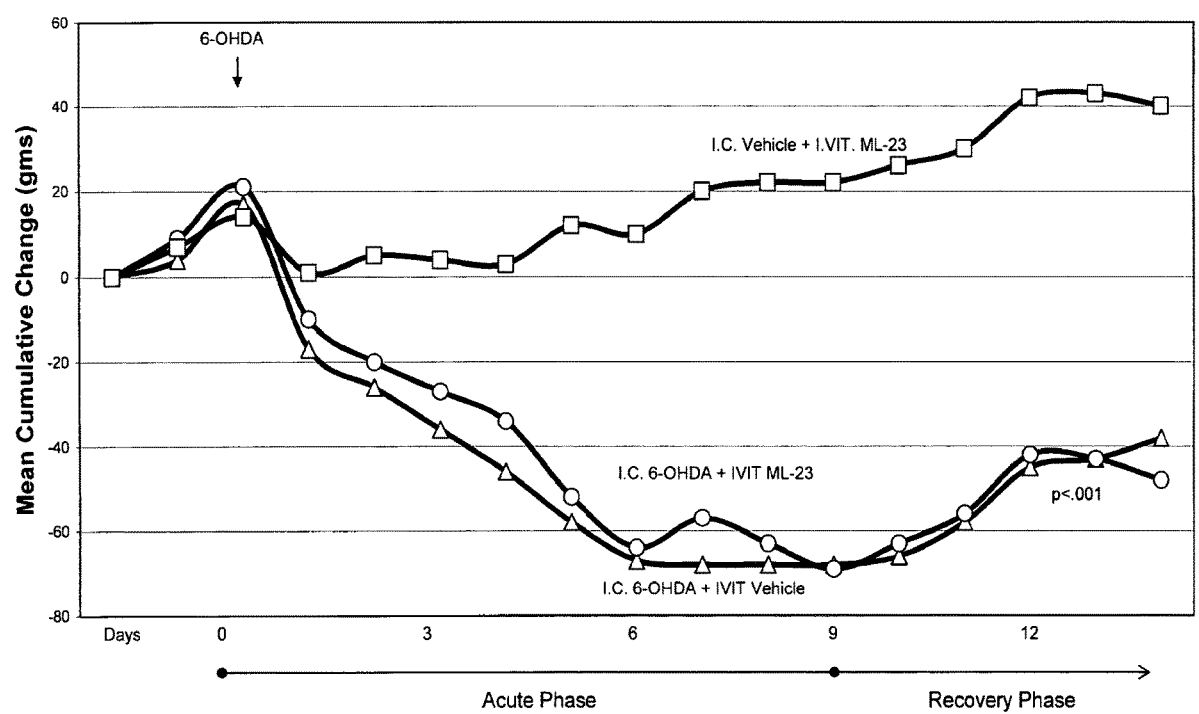
FIG. 13 is a graph showing the effect of intravitreal injection of ML-23 on body weight regulation in rats with experimental Parkinson's disease.

Psychosis in rats was induced by bilateral, intraocular or intravitreal injection of 2 µl of 12.5 µg/µl haloperidol into rats that had been pre-tested for 5 days prior with 1 mg/kg of dl-amphetamine. The rats were tested on latency to ambulate and latency to retract a limb As shown in FIG. 4, the administration of haloperidol increased both the latency to retract an elevated limb and the latency to ambulate from a prescribed area. Haloperidol is an anti-dopaminergic agent. As the release of dopamine plays a major role in the development of neuropsychiatric disorders such as schizophrenia, dyskinaesia, drug addiction and Huntington's Chorea, this indicates that therapeutic intervention at the level of the eye may be useful for treating these diseases. It is expected that other anti-psychotic agents are capable of producing a similar effect.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention claimed is:

1. A method for the treatment and/or prophylaxis of a patient suffering from Parkinson's disease or psychosis, comprising:
 administering to an eye of a patient who is suffering from Parkinson's disease or psychosis an agent in an amount effective for modulating levels of dopamine in a brain of the patient.

2. The method according to claim 1, wherein administering the agent comprises administering at least one of haloperidol, spiroperidol, thioxanthene, fluphenazine, lithium carbonate, thioidazine, diazepam, pimozide, chlorpromazine, benzodiazepines, respiradol, and quetiapine fumarate to the patient.

3. The method according to claim 1, wherein administering the agent comprises administering at least one of a dopamine precursor, a dopamine agonist, a dopamine degradative enzyme inhibitor to the patient.

4. The method according to claim 1, wherein administering the agent comprises administering at least one of melatonin and a melatonin analog to the patient.

5. The method according to claim 1, further comprising:
 administering one or more further agents sequentially, separately, or simultaneously with administering the agent.

6. The method according to claim 5, wherein administering the one or more further agents comprises administering the one or more further agents to the eye of the patient.

7. The method according to claim 1, further comprising:
 ocularly administering light therapy to the patient sequentially, separately, or simultaneously with administering to the eye of the patient the effective amount of the agent.

8. The method according to claim 7, wherein ocularly administering light therapy comprises ocularly administering broad spectrum white light to the patient.

9. The method according to claim 7, wherein ocularly administering light therapy comprises ocularly administering blue and/or green spectrum light to the patient.

10. The method according to claim 7, wherein ocularly administering light therapy occurs separately from administering to the eye of the patient the effective amount of the agent.

11. The method according to claim 1, wherein administering comprises administering the agent in a manner that enables the agent to come into contact with a retina of the eye.

12. The method according to claim 11, wherein administering comprises injecting the agent into the eye.

13. The method according to claim 12, wherein injecting the agent comprises injecting the agent into the vitreous humor of the eye.

14. The method according to claim 12, wherein injecting the agent comprises injecting the agent no more frequently than weekly.

15. The method according to claim 12, wherein injecting the agent comprises injecting the agent no more frequently than monthly.

16. A method for influencing dopamine function of a patient, comprising:
 administering to an eye of a patient an agent in an amount effective for modulating levels of dopamine in a brain of the patient.

17. The method of claim 16, further comprising:
 ocularly administering light to the patient.

18. The method of claim 17, wherein ocularly administering the light comprises ocularly administering blue and/or green spectrum light to the patient.

* * * * *